United States Patent [19]

Warwel et al.

[11] Patent Number: 5,143,885
[45] Date of Patent: Sep. 1, 1992

[54] CATALYSTS FOR THE METATHESIS OF OLEFINS AND FUNCTIONALIZED OLEFINS

[75] Inventors: Siegfried Warwel, Aachen; Hans-Gerd Jägers, Gladbeck; Andreas Deckers, Ludwigshafen, all of Fed. Rep. of Germany

[73] Assignee: Hüls Aktiengesellschaft, Marl, Fed. Rep. of Germany

[21] Appl. No.: 658,861

[22] Filed: Feb. 22, 1991

[30] Foreign Application Priority Data

Mar. 2, 1990 [DE] Fed. Rep. of Germany ....... 4006540

[51] Int. Cl.$^5$ .................. B01J 21/02; B01J 21/36; B01J 21/12; C07C 6/00

[52] U.S. Cl. .................. 502/202; 502/102; 502/241; 585/525; 585/647; 554/162; 554/163; 560/190

[58] Field of Search ................ 502/202, 241

[56] References Cited

U.S. PATENT DOCUMENTS

| | | | |
|---|---|---|---|
| 3,676,520 | 7/1972 | Heckelsberg | 585/647 |
| 3,925,249 | 12/1975 | Fitton et al. | 502/102 |
| 4,111,840 | 9/1978 | Best | 564/475 |
| 5,055,628 | 10/1991 | Lin et al. | 585/647 |

Primary Examiner—Paul E. Konopka
Attorney, Agent, or Firm—Oblon, Spivak, McClelland, Maier & Neustadt

[57] ABSTRACT

A catalyst for the metathesis of olefins and functionalized olefins, which contains a compound having the formula $B_2O_3$—$Re_2O_7/Al_2O_3$—$SiO_2$.

7 Claims, No Drawings

CATALYSTS FOR THE METATHESIS OF OLEFINS AND FUNCTIONALIZED OLEFINS

BACKGROUND OF THE INVENTION

1. Field of the Invention

The present invention relates to heterogeneous catalysts on an $Al_2O_3$—$SiO_2$ substrate for the metathesis of olefins and functionalized olefins.

2. Description of the Background

The metathesis of olefinic hydrocarbons is employed in the manufacture of specific olefins, dienes and polyenes and unsaturated polymers. Even olefins with functional groups are subject to the metathesis reaction, provided suitable catalysts are used. Of special importance is the metathesis of unsaturated fatty acid methyl esters, which are produced on large scale by transesterifying native fats and oils with methanol and are, thus, commercially available as parent compounds. The metathesis of these esters opens new simple access to intermediate products that are important from a chemical engineering point of view for the industrial production of surfactants, plastics, plasticizers, lubricants and a whole range of fine chemicals.

According to Bosma et al., *Journal of Organometallic Chemistry*, vol. 255 (1983), pp. 159-171, the metathesis of unsaturated esters can be performed on a $Re_2O_7$/$Al_2O_3$ catalyst, which is activated with an organo-tin compound of the general formula $SnR_4$. To manufacture the catalyst, $\gamma$-$Al_2O_3$ is impregnated with ammonium perrhenate.

Warwel, *Erdol-Erdgas-Kohle*, Petroleum, Natural Gas, Coal, vol. 103 (1987), pp. 238-45, describes industrial metathesis procedures, wherein predominantly $Re_2O_7$/$Al_2O_3$-, $CoO$-$MoO_3$/$Al_2O_3$ and $WO_3$/$SiO_2$ catalysts are used. Accordingly, only the $Re_2O_7$/$Al_2O_3$ catalyst is already active at room temperature.

According to FR 2 521 872, the metathesis of functionalized olefins can be performed on $Re_2O_7$/$Al_2O_3$—$SiO_2$ catalysts. The substrate contains preferably only 10 to 30% $SiO_2$. According to this process, organic lead compounds of the formula $PbR_4$ are used as activators.

In NL-A-84 03 051 the metathesis is preferably performed on $SiO_2$—rich supported catalysts. The $Re_2O_7$/$Al_2O_3$—$SiO_2$ catalysts contain in the substrate preferably 65 to 90% $SiO_2$. The activators used are preferably tin tetraethyl and tin tetrabutyl.

Unfortunately, in order to use catalysts effectively in metathesis reactions, it is, at present, necessary to use high concentrations or large amounts of catalysts. This is particularly true in the metathesis of unsaturated esters. In fact, there are no catalysts which are, at present, commercially feasible in the metathesis of unsaturated fatty acid esters.

SUMMARY OF THE INVENTION

Accordingly, it is an object of the present invention to provide a more effective catalyst for the metathesis of olefins and functionalized olefins.

It is also a particular object of this invention to provide a more effective catalyst for the metathesis of unsaturated fatty acid esters to provide higher conversions and higher yields.

The above objects and others which will become more apparent in view of the following disclosure are provided by a catalyst for the metathesis of olefins and functionalized olefins, which comprises a compound having the composition $B_2O_3$—$Re_2O_7$/$Al_2O_3$—$SiO_2$.

DETAILED DESCRIPTION OF THE PREFERRED EMBODIMENTS

In accordance with the present invention, catalysts are provided containing a compound having the formula $B_2O_3$—$Re_2O_7$/$Al_2O_3$—$SiO_2$. In these catalysts boron oxide and rhenium oxide are the compounds that act as the actual catalyst.

The aluminosilicate $Al_2O_3$—$SiO_2$ is the carrier. Surprisingly, it has been found that the catalyst action on an aluminosilicate carrier is higher than on either a $SiO_2$ or an $Al_2O_3$ carrier alone. In the carrier, the $SiO_2$ content ranges preferably from 20 to 50 percent by weight, however, a content ranging from 35 to 50 percent by weight is especially preferred.

The $B_2O_3$—$Re_2O_7$ content ranges from 2 to 30 percent by weight. At the same time, the $B_2O_3$ content can range from 1 to 20 percent by weight. The content ranges preferably from 2 to 10 percent by weight. The $Re_2O_7$ content fluctuates in the range of 1 to 20 percent by Weight. Two to 15 percent by weight of $Re_2O_7$ are preferred. The percents by weight are based on the aluminosilicate carrier.

To manufacture the present catalysts, the $Al_2O_3$—$SiO_2$ carrier is impregnated with a salt or another compound of the catalytically active elements. Thus, the carrier can be simultaneously impregnated with boric acid and ammonium perrhenate. After drying and heating, the oxidic catalyst is produced. However, one can also apply in succession first boric acid, then dewatering and transfer into the oxide and then impregnation with the rhenium salt, drying the rhenium salt and also transfer into the oxide.

The catalysts of the invention can be added as a powder, granulate or as a honeycomb. The catalysts are used preferably as a powder.

The $B_2O_3$—$Re_2O_7$/$Al_2O_3$13 $SiO_2$ catalysts are significantly more effective for metathetical reactions than known catalysts, which contain no $B_2O_3$ or, instead of an $Al_2O_3$—$SiO_2$ carrier, utilize a $\gamma$-$Al_2O_3$ carrier.

When olefin hydrocarbons are metathesized, no activator is required in addition to the catalysts of the invention. During the metathesis of functionalized olefins or during the co-metathesis of olefins and functionalized olefins the addition of an activator is, however, required.

Functionalized olefins, as specified by the invention, are unsaturated esters, esters, halogen and nitrogen compounds, aldehydes, ketones, and derived alcohols and derived carboxylic acids. Preferably, unsaturated carboxylates are added.

Suitable activators are organo-tin compounds, where tin tetraalkyl of the formula $SnR_4$ is preferred, where R is alkyl having 1 to 8 carbon atoms. Examples for R are methyl, ethyl, isopropyl and n-butyl.

Preferably, the activator is added in such quantities that the molar ratio of $Re_2O_7$:$SnR_4$ ranges from 5:1 to 1:5. In particular, a molar ratio ranging from 2:1 to 1:2 is preferred.

With the combination of $B_2O_3$—$Re_2O_7$/$Al_2O_3$—$SiO_2$ catalyst and $SnR_4$ activator, both pure olefin hydrocarbons and functionalized olefins, e.g., unsaturated carboxylic acid esters, can be metathesized, wherein in the latter case even at a molar ratio of $Re_2O_7$:ester of 1:1,000 high conversions can still be obtained. The metathetical reactions can be performed as homo-metathesis, as co-metathesis (use of two different olefinic compounds) and in the case of cycloolefins as the substrate as metathetical, ring-opening polymerization. The metathetical reactions are carried out preferably at room temperature, a state that is advantageous for reasons relating to energy conservation. However, the use of a lower or higher temperature is also possible.

The present invention will now be illustrated by reference to certain Examples which are provided for purposes of illustration and are not intended to be limitative.

EXAMPLE 1

Preparation of the catalyst $B_2O_3$—$Re_2O_7/Al_2O_3$—$SiO_2$

In a 250 ml single neck flask, 0.55 g of $NH_4ReO_4$ and 1.17 g of $H_3BO_3$ are dissolved in 135 ml of dioxan and 15 ml of $H_2O$. Following the addition of 10 g previously at 500° C. in an air current of calcinated aluminosilicate with 40 percent by weight of $SiO_2$, the entire mixture is heated at reflux overnight. Subsequently, the solvent is removed by distillation and the solid is predried in a water jet vacuum at b 130° C. The predried contact is heated to 500° C. in the air current and left at this temperature for 16 hours. Then, it is cooled to room temperature under argon. A $Re_2O_7$ content of 4.4 percent by weight and $B_2O_3$ content of 5.8 percent by weight is found by elementary analysis.

EXAMPLE 2

Co-metathesis of 10-undecenoic acid methyl ester with 4-octene

Catalyst: $B_2O_3$—$Re_2O_7/Al_2O_3$—$SiO_2$ + $Sn(n$—$C_4H_9)_4$

In a preheated 50 ml shaker flask filled with argon and comprising magnetic stirring cores, 0.5 g of the catalyst (with 0.045 mmol $Re_2O_7$) prepared in Example 1 are introduced and treated with 0.57 g (0.54 ml) of a $SnBu_4$ solution (0.1 molar in chlorobenzene, with 0.054 mmol $SnBu4$) and 1 ml of chlorobenzene. Then 8.06 g (11.23 ml) of 4-octene (72 mmol) and 7.13 g (8.03 ml) of 10-undecenoic acid methyl ester (36 mmol) are added, where the molar ratio of the individual components is as follows:

$Re_2O_7$:$SnBu_4$:$C_{11}$-ester:4-octene = 1:1.2:800:1,600

After stirring for 2 hours at room temperature, a sample is taken with a syringe and analyzed gas chromatographically following the addition of a few drops of methanol to decompose any catalyst residues.

According to the reaction equation:

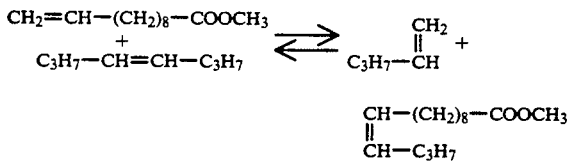

the reaction mixture contains, in addition to the parent compounds, 1-pentene and 10-tetradecenoic acid ester. Through homo-metathesis of 10-undecenoic acid ester, a small amount of unsaturated $C_{20}$-diester is also formed in accordance with the reaction:

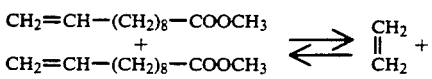

-continued $$\begin{array}{l}CH-(CH_2)_8-COOCH_3 \\ \| \\ CH-(CH_2)_8-COOCH_3\end{array}$$

The conversion of the added 10-undecenoic acid ester amounts to 77%. Of the regenerated esters, the $C_{14}$-monoester constitutes 87 percent by weight and the $C_{20}$-diester constitutes 13 percent by weight.

Comparison Example A

Co-metathesis of 10-undecenoic acid methyl ester with 4-octene

Catalyst: $Re_2O_7/Al_2O_3$—$SiO_2$ + $Sn(n$—$C_4H_9)_4$

The experiment from Example 2 is repeated; however, a $B_2O_3$-free catalyst is added. Compared to Example 2, the reaction conversion drops to 59%.

Comparison Example B

Co-metathesis of 10-undecenoic acid methyl ester with 4-octene

Catalyst: $B_2O_3$—$Re_2O_7$/gama—$Al_2O_3$ + $Sn(n$—$C_4H_9)_4$

The experiment from Example 2 is repeated; however, a $SiO_2$-free catalyst is added (exchange of aluminosilicate for $\gamma$-$Al_2O_3$). Compared to Example 2, the reaction conversion drops to 30%.

EXAMPLE 3

Co-metathesis of oleic acid methyl ester with 4-octene

Catalyst: $B_2O_3$—$Re_2O_7/Al_2O_3$—$SiO_2$ + $Sn(n$—$C_4H_9)_4$

In a preheated 50 ml shaker flask filled with argon and comprising magnetic stirring cores, 0.5 g of the catalyst (with 0.045 mmol $Re_2O_7$) prepared in Example 1 are introduced and treated with 0.57 g (0.54 ml) of a $SnBu_4$ solution (0.1 molar in chlorobenzene, with 0.054 mmol SnBu4) and 1 ml of chlorobenzene. Then 8.06 g of 4-octene (72 mmol) and 10.63 g of oleic acid methyl ester (36 mmol) are added, where the molar ratio of the individual components is as follows:

$Re_2O_7$:$SnBu_4$:oleic acid methyl ester:4-octene = 1:1.2:800:1,600

After a reaction period of 2 hours at room temperature, a sample is taken and analyzed gas chromatographically following the addition of a few drops of methanol to decompose any catalyst residues.

According to the reaction equation:

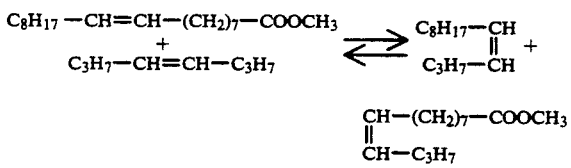

the reaction mixture now contains 4-tridecene and 9-tridecenoic acid ester. Through homo-metathesis of the oleic acid methyl ester according to the reaction:

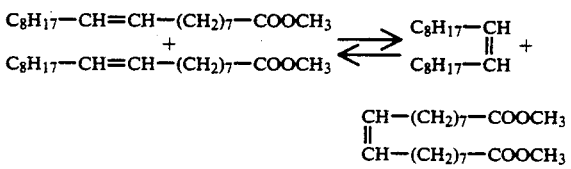

small amounts of 9-octadecene and 9-octadecenoic diacid dimethyl ester are also formed.

A reaction conversion of the added oleic acid methyl ester of 81% is found. The regenerated esters comprise 89 percent by weight of the unsaturated $C_{13}$-monoester and percent by weight of the unsaturated $C_{18}$-diester.

Comparison Example C

Co-metathesis of of oleic acid methyl ester with 4-octene

Catalyst: $Re_2O_7/Al_2O_3$—$SiO_2 + Sn(n$—$C_4H_9)_4$

The experiment from Example 3 is repeated; however, a $B_2O_3$-free catalyst is added. Now the conversion drops to 40%.

Comparison Example D

Co-metathesis of oleic acid methyl ester with 4-octene

Catalyst: $B_2O_3$—$Re_2O_7/gama$—$Al_2O_3 + Sn(n$—$C_4H_9)_4$

The experiment from Example 3 is repeated; however, a $SiO_2$-free catalyst is added. In addition, the concentration of catalyst and activator is nearly doubled. Now the molar ratio for $Re_2O_7$:$SnBu_4$ oleic acid methyl ester:4-octene = 1:1.5:500:1,000. Nevertheless, the conversion drops to 27%.

EXAMPLE 4

Homo-metathesis of 10-undecenoic acid methyl ester

Catalyst: $B_2O_3$—$Re_2O_7/Al_2O_3$—$SiO_2 + Sn(n$—$C_4H_9)_4$

In a preheated 50 ml shaker flask filled with argon and comprising a reflux condenser to which a bubble counter is attached, 0.5 g of the catalyst prepared in Example 1 are introduced and treated with 0.57 g (0.54 ml) of a $SnBu_4$ solution (0.1 molar in chlorobenzene) and 1 ml of chlorobenzene. Then 3.57 g 10-undecenoic acid methyl ester (18 mmol) are added, where the molar ratio of the individual components is as follows:

$Re_2O_7$:$SnBu_4$:$C_{11}$-ester = 1:1.2:400

After 2 hours at room temperature, a conversion of 49% is determined by means of gas chromatography. When the experiment is repeated at 80° C., a conversion of 60% is determined after 2 hours. In both experiments, according to

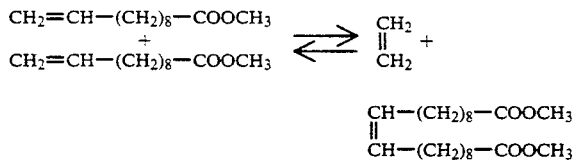

in addition of ethylene, 10-eicosenoic diacid methyl ester is formed exclusively.

EXAMPLE 5

Homo-metathesis of oleic acid methyl ester

Catalyst: $B_2O_3$—$Re_2O_7/Al_2O_3$—$SiO_2 + Sn(n$—$C_4H_9)_4$

In a preheated 50 ml shaker flask filled with argon and comprising magnetic stirring cores, 0.5 g of the catalyst prepared in Example 1 are introduced and treated with 0.57 g (0.54 ml) of a $SnBu_4$ solution (0.1 molar in chlorobenzene) and 1 ml of chlorobenzene. Then 5.32 g of oleic acid methyl ester (18 mmol) are added, where the molar ratio of the individual components is as follows:

$Re_2O_7$:$SnBu_4$:oleic acid methyl ester = 1:1.2:400

After 2 hours at 80° C., a 45% conversion of the oleic acid methyl ester to 9-octadecene and 9-octadecenoic diacid dimethyl ester according to the reaction:

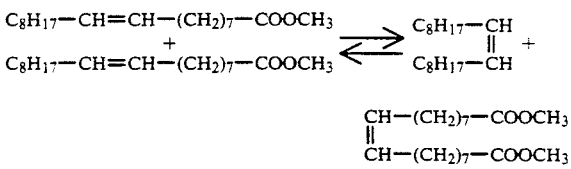

is obtained.

EXAMPLE 6

Co-metathesis of 4-octene with 5-decene

Catalyst: $B_2O_3$—$Re_2O_7/Al_2O_3$—$SiO_2 + Sn(n$—$C_4H_9)_4$

In a preheated 50 ml shaker flask filled with argon and comprising magnetic stirring cores, 1.6 g of the catalyst (with 0.146 mmol $Re_2O_7$) prepared in Example 1 are introduced and treated with 1.7 ml of a 1 molar $SnBu_4$ solution in chlorobenzene (with 0.173 mmol $SnBu_4$) and 1 ml of chlorobenzene. Then 13.1 g of 4-octene (116.8 mmol) and 16.4 g of 5-decene (116.8 mmol) are added, where the molar ratio of the individual components is as follows:

$Re_2O_7$:$SnBu_4$:4-octene:5-decene = 1:1.2:800:800.

After 2 hours at room temperature, a sample is taken and analyzed gas chromatographically. According to the reaction equation:

the reaction mixture contains, in addition to the feedstocks, also 4-nonene. The conversion of the added olefin is 50%; the selectivity for 4-nonene is 98%.

EXAMPLE 7

Co-metathesis of 4-octene with 5-decene

Catalyst: $B_2O_3$—$Re_2O_7/Al_2O_3$—$Si_2$

The experiment from Example 6 is repeated; however, no organo-tin activator is used. In this experiment, too, a 50% conversion is determined by means of gas chromatography with a selectivity for 4-nonene of 90%.

EXAMPLE 8

Homo-metathesis of 1-octene

Catalyst: $B_2O_3$—$Re_2O_7/Al_2O_3$—$Si_2 + Sn(n$—$C_4H_9)_4$

The experiment from Example 6 is repeated; however, instead of 4-octene and 5-decane, 1-octene is now added and the molar ratio of the individual components is set to $Re_2O_7$:$SnBu_4$:1-octene = 1:8:12,000.

After 3 hours at room temperature, a 42% conversion of 1-octene to ethylene and 7-tetradecene with a selectivity of 86% is determined by means of gas chromatography.

Having described the present invention, it will be apparent to one skilled in the art that many changes and modifications may be made to the above-described embodiments without departing from the spirit and scope of the present invention.

What is claimed as new and desired to be secured by letters patent of the United States is:

1. A catalyst for the metathesis of olefins and functionalized olefins, which consists essentially of $B_2O_3$—$Re_2O_7$ on an $Al_2O_3$—$SiO_2$ substrate, having a $Be_2O_3$—$Re_2O_7$ content of from 2 to 30% by wt., based on the $Al_2O_3$—$SiO_2$ content.

2. The catalyst of claim 1, wherein the $Re_2O_7$ content is from 1 to 20% by wt., based on the $Al_2O_3$—$SiO_2$ content.

3. The catalyst of claim 1, wherein the $B_2O_3$ content is from 1 to 20% by wt., based on the $Al_2O_3$—$SiO_2$ content.

4. The catalyst of claim 1, wherein the $SiO_2$ content is from 20 to 50% by wt., based on the $Al_2O_3$—$SiO_2$ content.

5. The catalyst of claim 4, wherein the $SiO_2$ content is from 35 to 50% by wt., based on the $Al_2O_3$—$SiO_2$ content.

6. The catalyst of claim 2, wherein the $Re_2O_7$ content is from 2 to 15% by wt., based on the $Al_2O_3$—$SiO_2$ content.

7. The catalyst of claim 3, wherein the $B_2O_3$ content is from 2 to 10% by wt., based on the $Al_2O_3$—$SiO_2$ content.

* * * * *